United States Patent [19]

Le Bec

[11] Patent Number: 4,825,802
[45] Date of Patent: May 2, 1989

[54] PHEUMATIC ALARM FOR RESPIRATOR

[75] Inventor: Yves Le Bec, Grigny, France

[73] Assignee: Societe Anonyme Drager, Paris, France

[21] Appl. No.: 120,368

[22] Filed: Nov. 13, 1987

[51] Int. Cl.$^4$ ............................................. F16K 37/00
[52] U.S. Cl. .................................. 116/70; 116/67 R; 137/557; 128/202.22
[58] Field of Search ............... 116/112, 70, 151, 67 R; 137/557; 128/202.22

[56] References Cited

U.S. PATENT DOCUMENTS

| | | | |
|---|---|---|---|
| 3,910,222 | 10/1975 | Metivier | 137/557 |
| 4,127,122 | 11/1978 | Kienhofer et al. | 128/142.5 |
| 4,176,617 | 12/1979 | Pilipski | 116/70 |
| 4,249,473 | 2/1981 | Pasternack et al. | 116/70 |
| 4,350,115 | 9/1982 | Pasternack | 116/70 |
| 4,474,175 | 10/1984 | Hudimac | 128/202.22 |
| 4,487,155 | 12/1984 | Olesen | 116/70 |

Primary Examiner—William M. Shoop, Jr.
Assistant Examiner—Brian K. Young
Attorney, Agent, or Firm—Herbert Dubno; Andrew Wilford

[57] ABSTRACT

An alarm system for a respirator fed from a supply of gas under pressure comprises a control valve having a pilot port and feed ports displaceable between an open position permitting fluid flow between the feed ports and a closed position preventing such flow. A pilot line connected to the pilot port is also operatively connected to the respirator for feeding gas under pressure from the respirator to the pilot port and urging the valve into one of the positions, the pressure in this pilot line being the pressure being applied to the patient. A spring is braced against the valve and urges same into the other position. A pneumatically actuatable acoustic alarm is connected to one of the feed port. Gas is fed substantially continuously under pressure to the other feed port. Thus when the pilot line pressure drops the valve moves into the other position and the alarm is either actuated or its actuation is stopped. Normally such a drop in pressure, which is indicative of equipment failure, the patient coming disconnected, or the supply running out, causes the valve to open and the alarm to sound.

5 Claims, 3 Drawing Sheets

PHEUMATIC ALARM FOR RESPIRATOR

FIELD OF THE INVENTION

The present invention relates to a pneumatic alarm for a pneumatic respirator. More particularly this invention concerns such an alarm which indicates some problem with the respirator and/or its functioning.

BACKGROUND OF THE INVENTION

It is advisable to equip a respirator with an audio and/or visual alarm that indicates when it is not operating properly. In particular it is necessary to raise an alarm when:
1. The patient becomes disconnected.
2. The pressure of the gas at the supply drops, for instance as a bottle runs out.
3. The respirator itself stops working from equipment failure.
4. The oxygen level in the incoming gas is insufficient.

In large fixed installations these alamrs are electrical or electronic. This is possible when a reliable source of electricity is present, but such electrically powered equipment is not recommended for use in the field, as in an ambulance or helicopter, because a battery must be provided and batteries are traditional sources of failure of portable equipment.

It is therefore advisable to use a pneumatically powered alarm for such portable equipment as if the equipment is operational it disposes of a source of gas under pressure. Unfortunately the only such alarms that are currently available are excessively complex and consume too much of the supply gas just to support the alarm function, even when in standby mode and not emitting an alarm. As a result portable equipment must either use a failure-prone electrical system or dispense with an alarm system altogether.

OBJECTS OF THE INVENTION

It is therefore an object of the present invention to provide an improved pneumatically powered alarm system for a respirator.

Another object is the provision of such a pneumatically powered alarm for a respirator which overcomes the above-given disadvantages, that is which is simple and failure-resistant, and which comsumes minimal gas when in standby.

SUMMARY OF THE INVENTION

An alarm system for a respirator fed from a supply of gas under pressure comprises a control valve having a pilot port and feed ports and displaceable between an open position permitting fluid flow between the feed ports and a closed position preventing such flow. A pilot line connected to the pilot port is also operatively connected to the respirator for feeding gas under pressure from the respirator to the pilot port and urging the valve into one of the positions, the pressure in this pilot line being the pressure currently being applied to the patient. A spring is braced against the valve and urges same into the other position. A pneumatically actuatable acoustic alarm is connected to one of the feed ports. Gas is fed substantially continuously under pressure to the other feed port. Thus when the pilot line pressure drops the valve moves into the other position and the alarm is either actuated or its acutation is stopped. Normally such a drop in pressure, which is indicative of equipment failure, the patient coming disconnected, or the supply running out, causes the valve to open and the alarm to sound.

Thus with the system of this invention the pressure of the system itself powers the acoustic alarm, but the device consumes no energy unless it is sounding an alarm. When the valve is closed there is no flow, so no gas is used.

According to another feature of this invention the acoustic alarm itself comprises a can forming a chamber, a diaphragm subdividing the chamber into two compartments one of which is vented and one of which is not, respective branch lines extending from the compartments to the one feed port of the control valve, a variable resistance in the branch line extending from the vented compartment, and a fixed resistance in the branch line extending from the unvented compartment. This diaphragm will vibrate in accordance with the pressure differential created across it and make a distinctive sound.

In accordance with another feature of this invention the system has a pressure amplifier or relay connected in the pilot line and to the supply for amplifying the pressure detected at the respirator and applying the amplified pressure to the other feed port and a pressure accumulator connected in the pilot line between the amplifier and the control valve. This system can further be equipped with a pneumatically powered visible alarm and a valve connected to the visible alarm, to the respirator, and to the accumulator for operating the visible alarm as the respirator operates and the pressure in the accumulator drops below a predetermined threshold. A pneumatic AND gate with an inverted input operates the visible alarm.

This last-described system can further be provided with another accumulator connected between the supply and the other feed port of the control valve and a cutout for venting and preventing pressurization of the other accumulator, thereby cutting out the acoustic alarm. This cutout is useful to silence the alarm which otherwise sounds automatically on startup.

DESCRIPTION OF THE DRAWING

The above and other objects, features, and advantages will become more apparent from the following, it being understood that any feature described with reference to one embodiment of the invention can be used where possible with any other embodiment and that reference numerals not specifically mentioned with reference to one figure but identical to those of another refer to structure that is functionally if not structurally identical. In the accompanying drawing.

SPECIFIC DESCRIPTION

Figure 1:
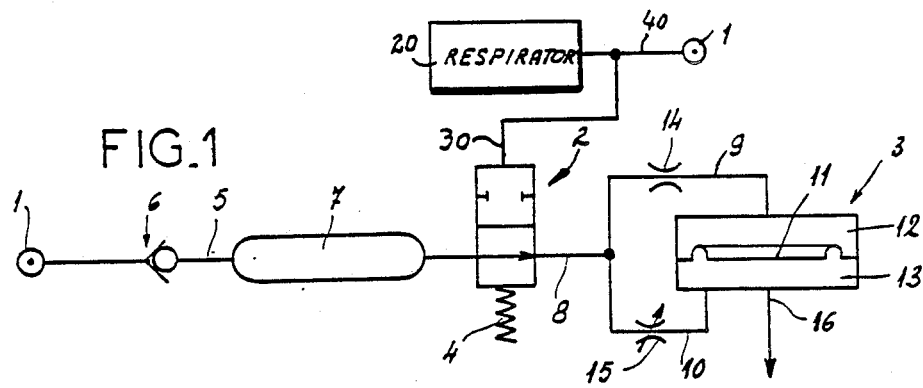
FIG. 1 is a schematic view of the alarm of the present invention while sounding an alarm.
Figure 2:
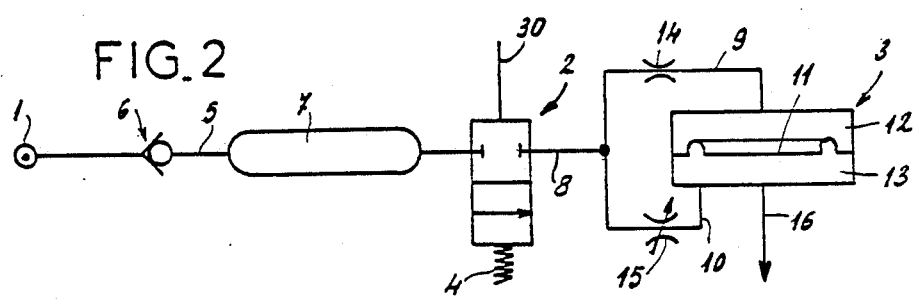
FIG. 2 is the system of FIG. 1 in the standby position not sounding an alarm.

As seen in FIGS. 1 and 2 a supply 1 of gas under pressure is connected via a main feed line 40 to a respirator 20. The pressure in the line 40 and in the respirator 20 are substantially identical. A pilot line 30 extends from the line 40 to the pilot port of a fast-action control valve 2 biased into the open position by a spring 4. Thus when the pneumatic force in the pilot compartment of the valve 2 exceeds the force of the spring 4, the valve 2 will move rapidly from the open position of FIG. 1 to the closed position of FIG. 2. In the open position the valve 2 connects an acoustic alarm 3 to the supply 1 or to another similar supply.

The valve 2 therefore has an input feed port connected via a line 5 to the supply 1. A check valve 6 prevents any flow back to the supply 1 and a small pressure accumulator 7 in the line 5 buffers the pressure fed to the valve 2. The output feed port of the valve 2 is connected to a line 8 that branches at 9 and 10 to feed opposite sides of the alarm 3 which is a closed can subdivided by a flexible diaphragm 11 into two compartments 12 and 13 into which the branches 9 and 10 open, respectively. The branch 9 is provided with a fixed flow restriction 14 and the line 10 with a variable restriction 15. The compartment 13 is vented at 16.

Thus when as seen in FIG. 1 there is insufficient pressure in the line 40, indicating either that the patient has become disconnected or the supply 1 is running out, the spring force will be able to overcome the pressure from the pilot line 30 and the valve 2 will open. Gas under pressure will flow from the source 1 through the line 5, valve 2, and line 8 to the two branches 9 and 10 which will apply it as a differential pressure across the diaphragm 11 to cause it to vibrate. The strength of the vibrations is adjusted by varying the restriction 15.

Figure 4:
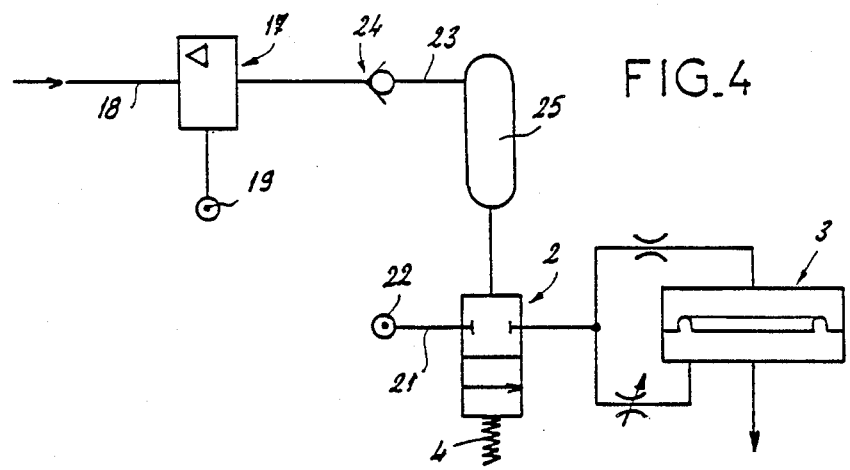

When, however, pressure in the lines 40 and 30 is sufficient, the valve 2 is held closed as shown in FIG. 4. This completely depressurizes the alarm 3 so it is silent. The accumulator 7 is sufficiently large that it alone can sustain the alarm for 7 sec to 10 sec. Thus even if the supply 1 fails altogether, the alarm will still have enough power of its own left ot operate.

Figure 3:
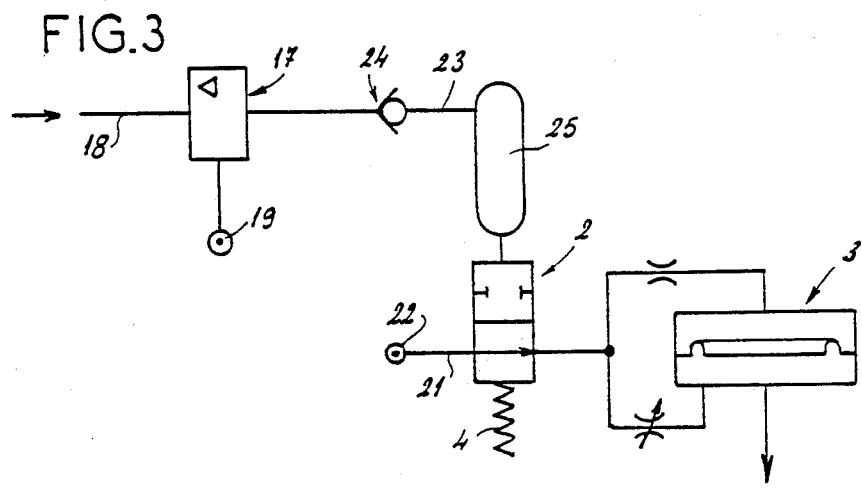
FIGS. 3 and 4 are views corresponding to respective FIGS. 1 and 2 but showing the system further equipped with a pressure amplifier.

In the system of FIG. 3 a pilot line 18 equivalent to the line 30 is connected to a pressure amplifier 17 itself connected via a line 23 containing a check valve 24 and an accumulator 24 to the pilot port of the valve 2, and to a supply 19 of gas pressurized tolbar to −10 bar. In this case the valve 2 is connected directly at its input feed port via a line 21 to another supply 22 or the same one.

With each inhalation of the patient connected to the respirator 20 being monitored by this device the amplifier 17 delivers an output pressure of about 1.5 bar. This pressure, once it has pressurized the bottle 25, is sufficient to hold the valve 2 closed and keep the alarm silent as shown in FIG. 4. On subsequent exhalation the amplifier 17 produces nothing, but the pressure stored in the bottle 25 is available to keep the valve 2 closed. Normal periodic inhalation by the patient connected to the respirator is sufficient to keep the accumulator 25 pressurized and the valve 2 closed.

A particular advantage of this arrangement is that it self tests whenever it is started up. Presuming the system is completely depressurized, even when working perfectly it will take a few seconds before the bottle 25 is sufficiently pressurized to close the valve 2 and hold it closed. Thus during such startup the acoustic alarm 3 will sound, indicating that it works.

Figure 5:
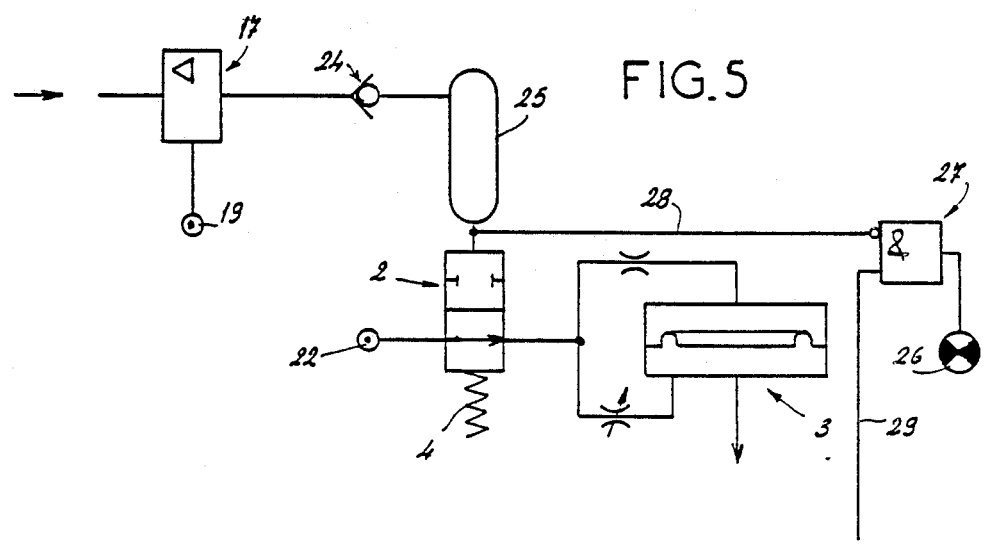
FIGS. 5 and 6 correspond respectively to FIGS. 3 and 4 and show the system further provided with a visual warning device.
Figure 6:
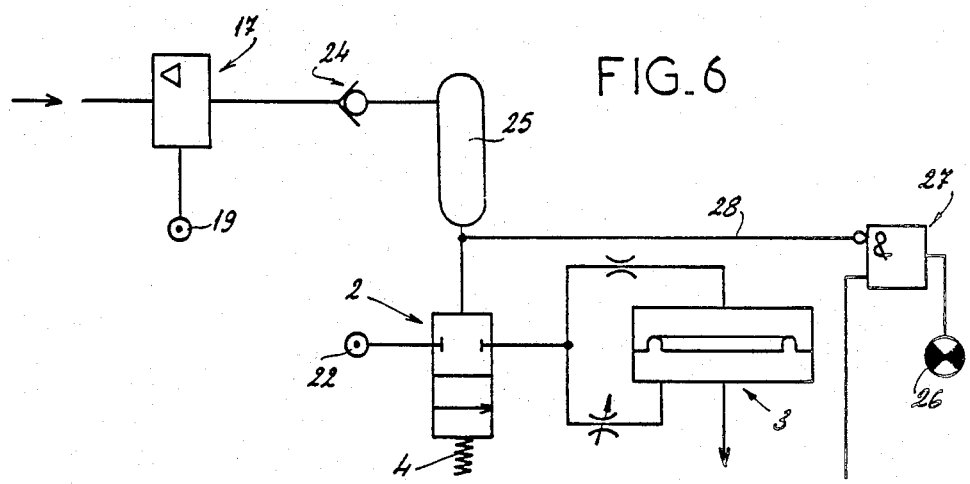

A variation on the system of FIGS. 3 and 4 is shown in FIGS. 5 and 6. Here an addition visual alarm 26 is provided that is connected via a pneumatic AND gate 27 having one input connected via an inverter to a line 28 fed from the supply 25 and an uninverted input connected via a line 29 to the respirator. When the pressure in the accumulator 25 remains high, the alarm 26 will be quiescent, that is not move, but when, for example, the patient becomes disconnected, the pressure drops in the line 28, the alarm 26 will be actuated synchronously as the patient breathes, as detected through the sensor line 29.

This arrangement has several advantages:
1. The visible alarm 26 is noticed under virtually any circumstances, even in noisy environments such as in a medical-emergency relief helicopter.
2. The alarm 26 does not use any gas as it is operated.
3. The system automatically tests itself on startup, that is the alarm goes off until the bottle 25 is pressurized which takes a few seconds even when the system is operating perfectly.

Figure 7:
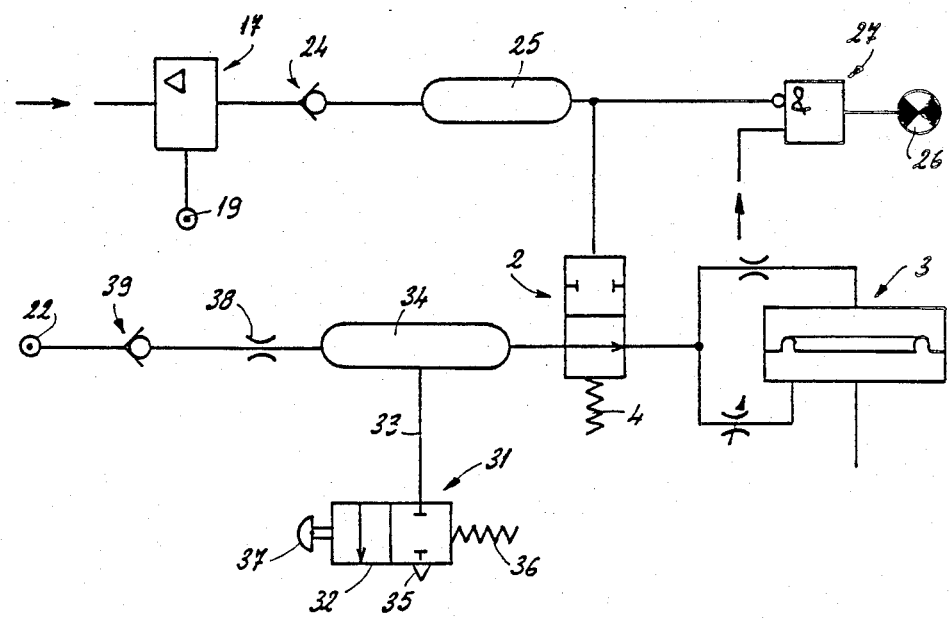
FIG. 7 is a view like FIG. 5 but showing the system provided with an acoustic-alarm shutoff.

The system of FIG. 7 is identical to that of FIGS. 5 and 6 except that it is provided with a cutout device 31 that can override the acoustic alarm. To this end a restriction 38 is provided in the line between the intake feed port of the valve 2 and a check valve 39 is provided immediately upstream and an accumulator 34 immediately downstream. Thus under normal circumstances the restriction 38 will allow slow pressurizing and charging of the accumulator 34 which itself supplies the pressurized gas used to sound the alarm 3.

The bottle 34 has a vent 33 that can either be closed or connected to another vent 35 by a valve 32 of the cutout 31. A spring 36 normally holds the valve 32 closed and an oppositely effective button 37 can open it. Thus when the acoustic alarm is to be bypassed, as for instance on startup, the button 37 is pressed to vent the accumulator 34 until pressure has built up sufficiently to close the valve 2. Then the valve 32 is allowed to close so that the system can pressurize upstream of the control valve 2.

I claim:
1. An alarm system for a respirator fed from a supply of gas under pressure, the system comprising:
   a control valve having a pilot port, an alarm port, and an input port and displaceable between an open position permitting fluid flow between the alarm and input ports and a closed position preventing such flow;
   a pilot line connected to the pilot port and operatively connected to the respirator for feeding pressure from the respirator to the pilot port and urging the valve into the closed position;
   a spring braced against the valve and urging same into the open position;
   a pneumatically actuatable acoustic alarm connected to the alarm port and comprising
      a chamber;
      a diaphragm subdividing the chamber into two compartments, one of the compartments being vented and the other unvented;
      respective branch lines extending from the compartments to the alarm port of the control valve;
      a variable resistance in the branch line extending from the vented compartment; and a fixed resistance in the branch line extending from the unvented compartment; and means for feeding gas under pressure substantially continuously to the input port, whereby when the pilot line pressure drops the valve moves into the open position and the alarm is actuated.

2. The alarm system defined in claim 1, further comprising:

a pressure amplifier connected in the pilot line and to the supply for amplifying the pressure detected at the respirator and applying the amplified pressure to the input port of the valve; and a pressure accumulator connected in the pilot line between the amplifier and the control valve.

3. The alarm system defined in claim 2, further comprising:

a visible pneumatically powered alarm; and valve means connected to the visible alarm, to the respirator, and to the accumulator for operating the visible alarm as the respirator operates and the pressure in the accumulator drops below a predetermined threshold.

4. The alarm system defined in claim 3, further comprising:

another accumulator connected between the supply and the input port of the control valve; and cutout means for venting and preventing pressurization of the other accumulator, thereby overriding the acoustic alarm.

5. An alarm system for a respirator fed from a supply of gas under pressure, the system comprising:

a control valve having a pilot port, an input port, and an alarm port and displaceable between an open position permitting fluid flow between the alarm and input ports and a closed position preventing such flow;

a pilot line connected to the pilot port and operatively connected to the respirator for feeding pressure from the respirator to the pilot port and urging the valve into the closed position;

a spring braced against the valve and urging same into the open position; and a pneumatically actuatable acoustic alarm connected to the alarm ports, the input port being connected to the supply, whereby when the pilot line pressure drops the valve closes and the alarm sounds.

* * * * *